United States Patent [19]

Hay et al.

[11] Patent Number: 5,359,092
[45] Date of Patent: Oct. 25, 1994

[54] BIS-N-AMINOIMIDES

[76] Inventors: Allan S. Hay, 5015 Glencairn Avenue, Montreal, Quebec, Canada, H3W 2B3; Hossein Ghassemi, 3440 Durocher Street, Apt. 1503, Montreal, Quebec, Canada, H2X 2E2

[21] Appl. No.: 70,246

[22] Filed: Jun. 2, 1993

[51] Int. Cl.⁵ .................. C07D 209/48; C07D 221/06
[52] U.S. Cl. ......................... 546/99; 546/37; 546/66; 548/461
[58] Field of Search ............... 546/37, 66, 99; 548/461

[56] References Cited

U.S. PATENT DOCUMENTS 2,816,897  12/1957  Wolf .................. 564/148 X
3,965,125  6/1976  Meyers ............... 260/346.3

FOREIGN PATENT DOCUMENTS 1337225  11/1973  United Kingdom .

OTHER PUBLICATIONS

Schuetz et al, Chemical Abstracts, vol. 66 (1967) 65334u.
Dine-Hart, Chemical Abstracts, vol. 69 (1968) 77839n.
Schuetz et al, Chemical Abstracts, vol. 75 (1971) 97046d.
Dine-Hart, Chemical Abstracts, vol. 76 (1972) 154304h.
Gangneux et al, Chemical Abstracts, vol. 79 (1973) 92638w.
Gangneux et al, Chemical Abstracts, vol. 79 (1973) 93421g.
Gangneux et al, Chemical Abstracts, vol. 80 (1974) 49064q.
Jankowski et al, Chemical Abstracts, vol. 85 (1976) 48251q.
Papenfuhr et al, Chemical Abstracts, vol. 85 (1976) 178962h.
Schuetz et al, Chemical Abstracts, vol. 90 (1979) 205789u.
Troy et al, Chemical Abstracts, vol. 104 (1986) 34410q.
Topics in Applied Chemistry "High-Technology Applications of Organic Colorants", Peter Gregory, 1991, pp. 10-11, 16-21, 76-79, 108-109.
Chemiluminescent Organic Compounds, Part I H. D. K. Drew et al, pp. 16-26 (submitted Apr. 1936.
Chemiluminescent Organic Compounds, Parts II & III, H. D. K. Drew et al, pp. 26-37. (submitted Oct. 1936).
Chemiluminescent Organic Compounds, Part IV, H. D. K. Drew et al pp. 586-592 (submitted Feb. 1937).
J. Chem. Soc. Perkin Trans. 2, 1992, Michael S. Alexiou et al, pp. 837-842.
J. Chem. Soc. (c), 1969, F. K. Badder et al, pp. 838-840.

*Primary Examiner*—Richard L. Raymond
*Attorney, Agent, or Firm*—Swabey Ogilvy Renault

[57] ABSTRACT

Bis-N-aminoimides of formula (III):

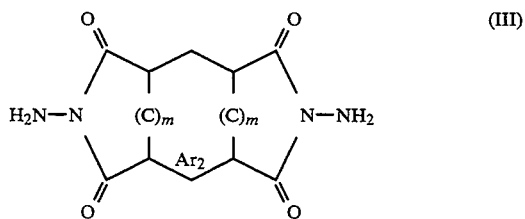

wherein m is 0 or 1 and $Ar_2$ is a mono- or polycyclic aromatic radical, can be employed to produce a variety of polymers of the type produced from diamines, including polyimides having an N—N linkage; polymers can be produced having exceptionally high glass transition temperatures, but which are also soluble in organic solvents; coloured polymers and electroconductive polymers and photoconductive polymers can also be produced.

10 Claims, No Drawings

BIS-N-AMINOIMIDES

BACKGROUND OF THE INVENTION

1. Field of the Invention

This invention relates to new bis-N-aminoimides and their preparation; polymers derived from the new bis-N-aminoimides; and polyimides having an N—N linkage and their preparation; the invention is also concerned with new diimides.

2. Description of Prior Art

In a study of chemiluminescent organic compounds H. D. K. Drew and H. H. Hiatt (J. Chem. Soc. 16, (1937)) found that the reaction of hydrazine with phthalic anhydride can yield the N-aminophthalimide as well as phthalhydrazide:

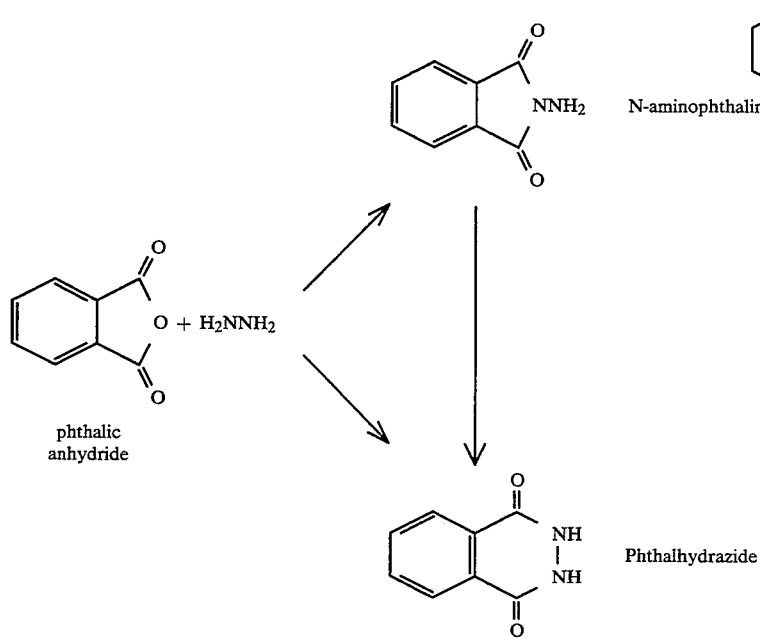

A maximum yield of about 50% of N-aminophthalimide was obtained when the reaction was carried out over a short period of time, and this readily converts to phthalhydrazide. They found that N-aminophthalimide reacts with phthalic anhydride in almost quantitative yield to give the diimide which is a stable compound, mp 311°–313° C.

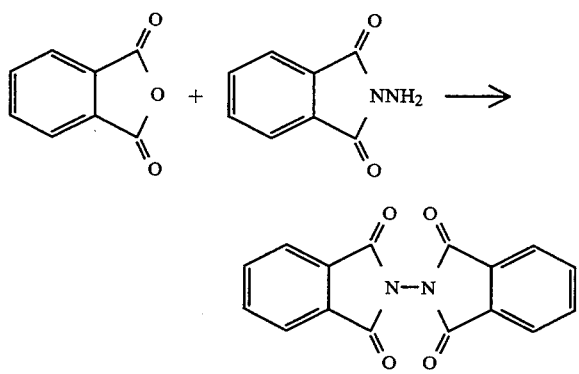

Subsequently they reported (H. D. K. Drew and F. H. Pearman, J. Chem. Soc. 26, (1937); H. D. K. Drew and F. H. Pearman, J. Chem. Soc. 586, (1937)) that with substituents in the 3- and 6-positions (a. 3-chloro, b. 3,6-dichloro, c. 3-amino-, d. 3,6-diamino-) that the N-aminophthalimide could be selectively formed. Presumably with substituents flanking the imide moiety and providing some steric hindrance the 5-membered ring in the N-aminophthalimide is preferred.

Later it was found (F. G. Baddar, M. F. El-Newaihy and M. R. Salem, J. Chem. Soc. 838, 1969) that in the reaction of 1-phenylnaphthalene-2,3-dicarboxylic anhydride (R=H in formula (XXX))

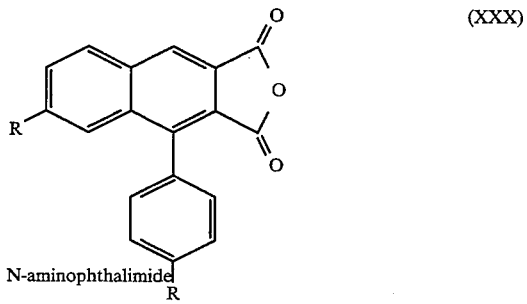

with hydrazine that a mixture of the N-amino compound and the phthalazine-1,4-dione were obtained. The 4'-7-dimethoxy anhydride (R=OMe) however gave the N-amino compound.

It has also been reported (M. S. Aleziou, V. Tychopoulos, S. Ghorbanian, J. H. P. Tyman, R. G. Brown and P. I. Brittain, J. Chem. Soc. Perkin Trans. 2, 837 (1990)) that hydrazine reacts with 4-nitro-1,8-naphthalic anhydride to give the N-amino compound:

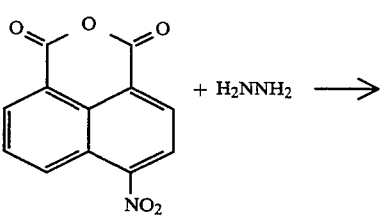

and Ultem ® is synthesized from bisphenol A dianhydride and m-phenylene diamine:

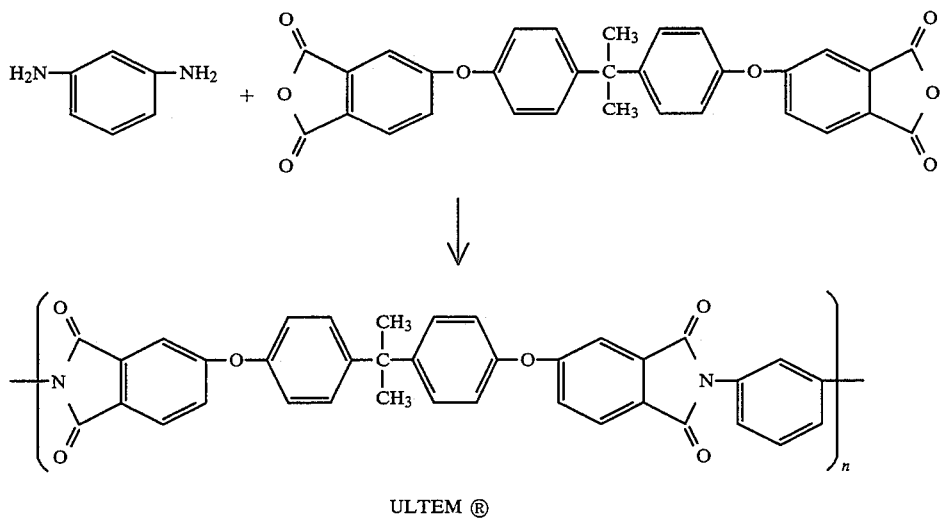

ULTEM ®

Polyimides are an important class of polymers noted for their exceptional thermal stability and solvent resistance. They are commonly synthesized by the reaction of dianhydrides with aliphatic or aromatic diamines. For example, Kapton ® is synthesized from pyromellitic dianhydride and oxydianiline

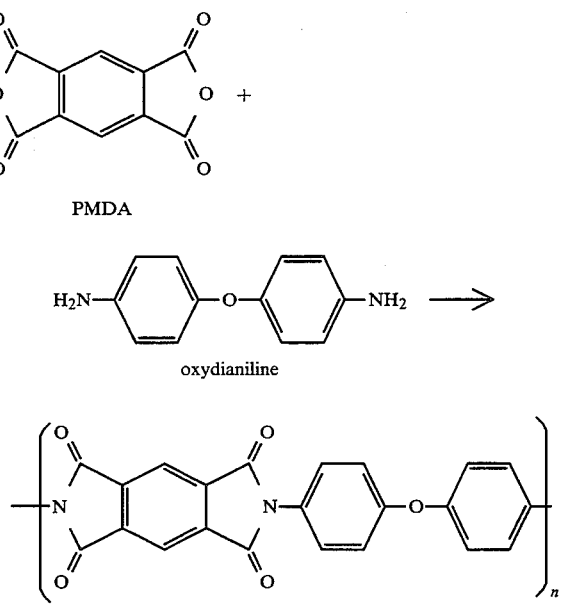

Kapton ®

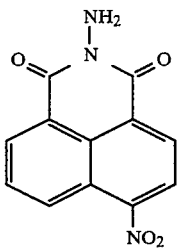

30

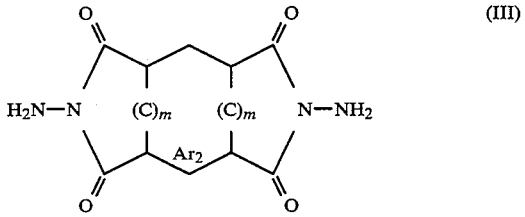

NO₂ 35

It is desirable to produce polymers of high glass transition temperature, especially such polymers which are soluble, so that polymer films and coatings of high glass transition temperature polymers can be produced from solution.

SUMMARY OF THE INVENTION

It is an object of this invention to provide novel bis-N-aminoimides which can be used in the preparation of polymers.

It is a further object of this invention to provide a process for producing the novel bis-N-aminoimides.

It is still another object of this invention to provide novel polymers derived from the bis-N-aminoimides.

It is a specific object of this invention to provide polyimides having an N—N linkage.

It is yet another object of this invention to provide novel diimides useful for preparing polymers.

In accordance with the invention there is provided bis-N-aminoimides of formula (III):

$$\text{H}_2\text{N}-\text{N} \quad (C)_m \quad (C)_m \quad \text{N}-\text{NH}_2 \quad \text{Ar}_2 \tag{III}$$

wherein m is 0 or 1 and $Ar_2$ is a mono- or polycyclic aromatic radical.

In another aspect of the invention there is provided a process for producing the bis-N-aminoamides (III) by reacting a dianhydride with hydrazine.

In still another aspect of the invention there is provided polymers of formula (I):

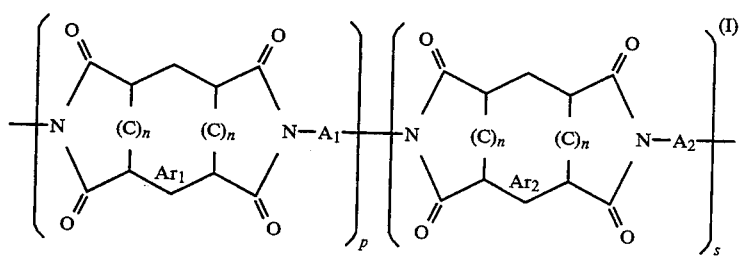

wherein $A_1$ is a radical of formula (V):

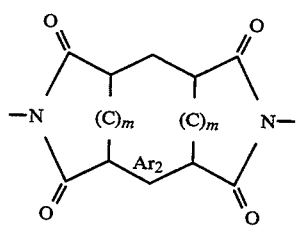

and $A_2$ is selected from radicals of formula (V) and radicals of formula (VI):

—R—  (VI)

n is an integer of 0 or 1,
m is an integer of 0 or 1,
$Ar_1$ and $Ar_2$ are independently selected from mono- and polycyclic aromatic radicals;
R is an arylene or alkylene radical,
p is an integer of 1 to 100,
s is an integer of 0 to 100, and
p+s is an integer of 2 to 100.

In yet another aspect of the invention there is provided a polymer of formula (VII):

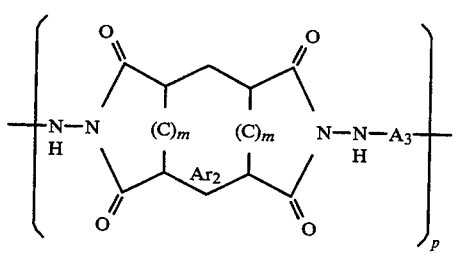

wherein
m is an integer of 0 to 1,
p is an integer of 2 to 100,
$Ar_2$ is a mono- or polycyclic aromatic radical, and
$A_3$ is a radical selected from

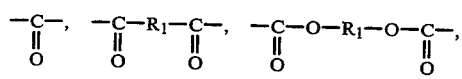

in which $R_1$ is arylene or alkylene.

In a still further aspect of the invention there is provided polymers of formula (II):

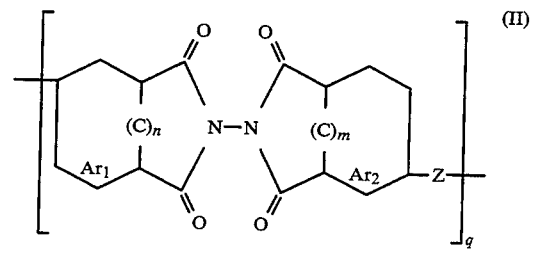

wherein
m is an integer of 0 or 1,
n is an integer of 0 or 1;
q is an integer of 2 to 100,
$Ar_1$ and $Ar_2$ are independently selected from mono- and polycyclic aromatic radicals; and
Z is a bisphenol or biphenol linking radical.

In still further aspects of the invention there are provided polymerization processes for preparing the polymers (I), (II) and (VII) hereinbefore described.

In another aspect of the invention there is provided a diimide of formula (IX):

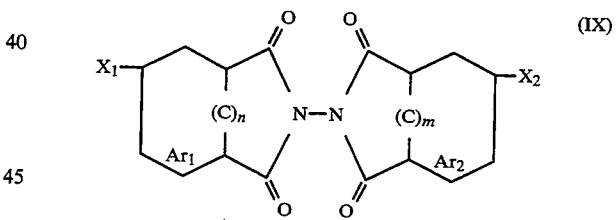

wherein m, n, $Ar_1$ and $Ar_2$ are as defined hereinbefore, and and $X_1$ and $X_2$ are the same or different and are selected from F, Cl, Br and $NO_2$.

DESCRIPTION OF PREFERRED EMBODIMENTS a) Bis-N-aminoimides

In the bis-N-aminoimides of formula (III), the fused radical $Ar_2$ may comprise a monocyclic aromatic nucleus, for example, benzene, in a phthalimide type structure, in which case m is 0; or a polycyclic aromatic nucleus which may comprise 2 or more fused aromatic rings or 2 or more non-fused aromatic rings. In the case of non-fused aromatic rings the aromatic rings may be separated by divalent linkages, for example, bisphenol-type linkages or biphenol-type linkages.

In the case of a polycyclic aromatic nucleus this may comprise groups of 2 or more fused aromatic rings separated by the afore-mentioned divalent linkages.

By way of example, bis-N-aminoimides of formula (III) include the following:

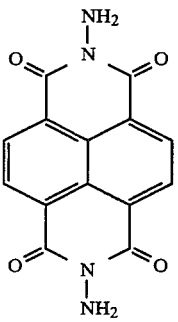

XI

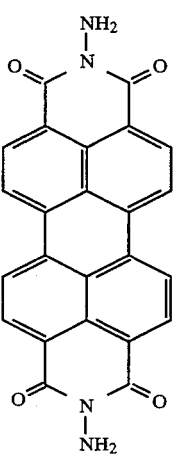

XII

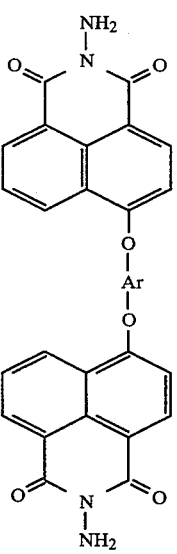

XIII and

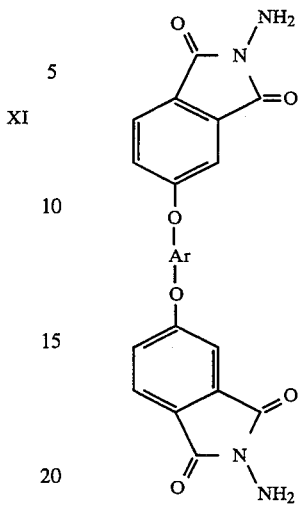

XIV in which O—Ar—O in XIII and XIV is a bisphenol or biphenol-type linkage, typically having 12 to 27 carbon atoms.

The bis-N-aminoimides (III) of the invention can be employed in reactions in which diamines are employed, to produce novel products with novel characteristics, for example, they may be reacted with phosgene or diisocyanates to produce polyureas, with dicarboxylic acids or diacid chlorides such as terephthaloyl or isophthaloyl chloride to produce polyamides, and with bis-chloroformates to produce polyurethanes.

Furthermore, the bis-N-aminoimides (III) may be reacted with dianhydrides to produce polyimides and by additionally reacting diamines with the dianhydrides and the imides (I), new polyimide copolymers may be obtained.

b) Preparation of bis-N-aminoimides

The bis-N-aminoimides (III) may be prepared from corresponding dianhydrides by reaction with hydrazine as illustrated below:

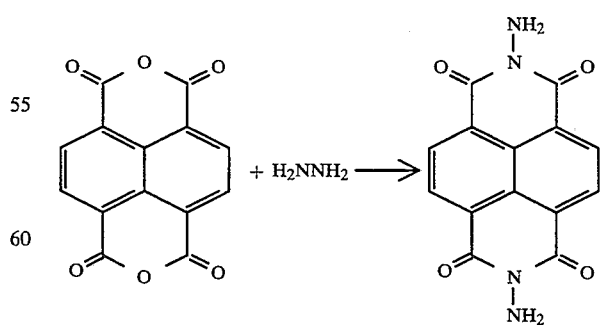

More especially the bis-N-aminoimides (III) are prepared by reaction of hydrazine with a dianhydride of formula (IV):

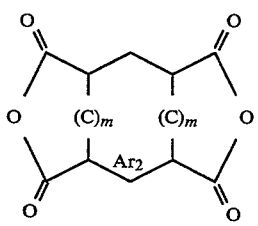 (IV)

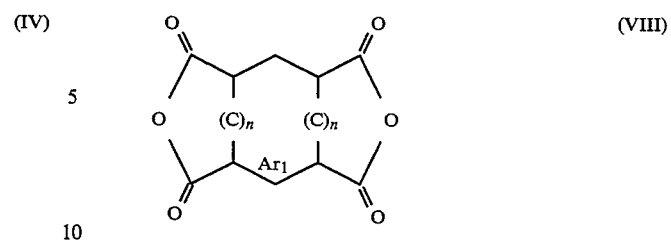 (VIII)

wherein m and Ar₂ are as described hereinbefore.

c) Polyimides

The polyimides (I) of the invention may be considered homopolymers when $A_1$ and $A_2$ are identical radicals of formula (V), and copolymers when $A_2$ is a radical of formula (VI).

The fused radical Ar₂ is selected from the same class as described for Ar₂ hereinbefore.

The arylene radical R suitably contains 6 to 10 carbon atoms, for example, phenylene or naphthylene and may be unsubstituted or substituted with one or more of lower alkyl or lower alkoxy of 1 to 6 carbon atoms, haloalkyl of 1 to 6 carbon atoms in which the halo is fluoro, chloro or bromo and halogen, for example, fluorine or chlorine.

The alkylene radical R suitably contains 1 to 10 carbon atoms and is a straight or branched chain radical.

The polyimides (I) are particularly characterized by an N—N linkage.

d) Preparation of Polyimides

The polyimides (I) are produced by polymerizing a dianhydride of formula (VIII):

wherein n is an integer of 0 or 1, and

Ar₁ is a mono- or polycyclic aromatic radical as described hereinbefore, with at least one diamine selected from diamines of formulae:

$$H_2N—A_1—NH_2 \text{ and } H_2N—A_2—NH_2$$

wherein $A_1$ and $A_2$ are as defined hereinbefore.

If $A_2$ is the radical (VI), a copolymer is produced, and the relative proportions of the two diamines determine the values of p and s.

By way of example bis(N-amino)imides (III) of the formula XI, XII and XIII as described hereinbefore have been employed to produce polyimides and polyimide copolymers by reaction with dianhydrides or a mixture of dianhydrides. Alternatively the copolymers may be produced by reaction bis(N-amino)imides (III) and diamines of formulae $$H_2N—A_1—NH_2 \text{ and } H_2N—A_2—NH_2$$

with one or more dianhydrides of formula (VIII). Table I below shows the properties of polymers synthesized from XIII in which O—A—O is a bisphenol A radical, in accordance with the following scheme:

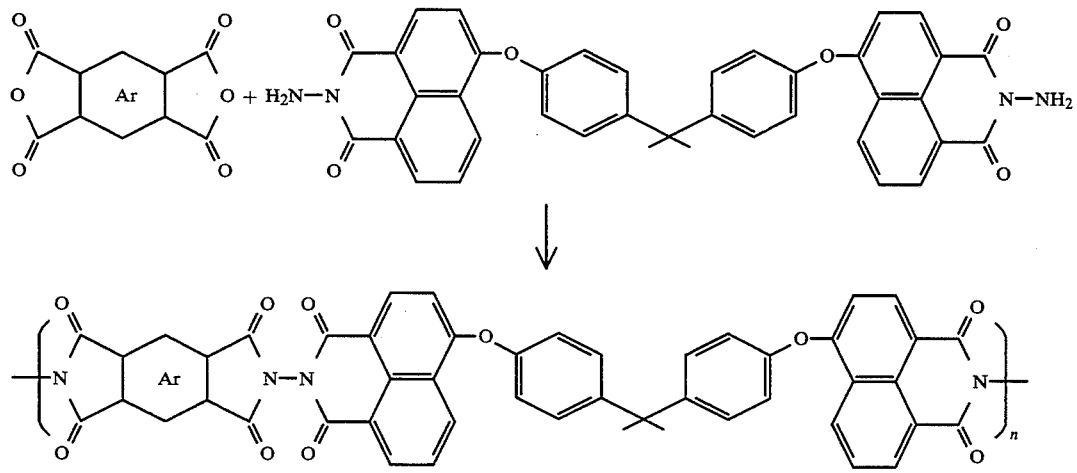

TABLE I

| Anhydride | Tg (°C.) | tan δ (max) (°C.) | Young's modulus (GPa) at 25° C. | Young's modulus (GPa) at 200° C. | TGA (°C.) N2 | TGA (°C.) air | Solubility |
|---|---|---|---|---|---|---|---|
| PMDA | ND | 380 | 2.22 | 1.92 | 455 | 457 | NMP, o-DCB |
| ODPA | 357 | 340 | 1.81 | 1.48 | 470 | 477 | NMP, PhCl |
| BTDA | 360 | 345 | 2.06 | 1.67 | 454 | 475 | NMP, o-DCB |
| SDA | 362 | 352 | 2.52 | 2.03 | 452 | 466 | NMP, o-DCB |
| BPADA | 307 | 291 | 0.72 | 0.68 | 474 | 467 | CHCl₃ |
| BPDA | 375 | 366 | 2.08 | 1.81 | 468 | 478 | NMP, o-DCB |

The glass transition temperatures of these polymers are remarkably high especially considering that the polymers are still soluble.

Polyimides prepared from BPF (Fluorene-bisphenol) have even higher glass transition temperatures and remarkably they maintain their physical properties up to 370° C. as indicated by the modulus measurements at 370° C.

PMDA
Pyromellitic Dianhydride

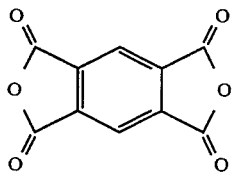

ODPA
Oxy-Di-4-Phthalic Anhydride

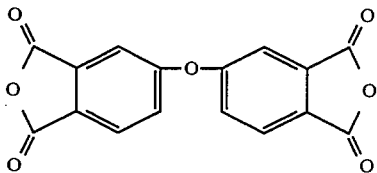

BTDA
Benzophenone Tetracarboxylic Dianhydride

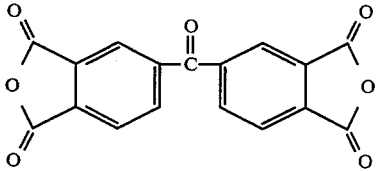

SDA
Sulfone-Bis-Phthalic Anhydride

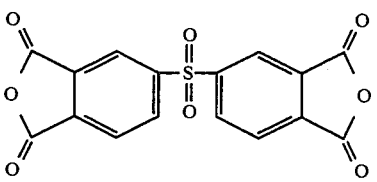

BPADA
BPA Diphthalic Anhydride

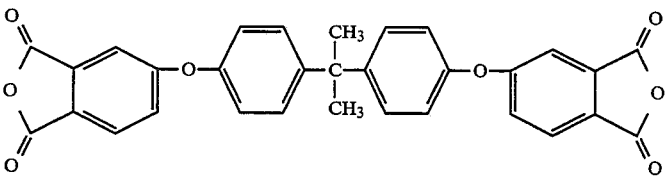

BPDA
3,3',4,4'-Biphenyl Dianhydride

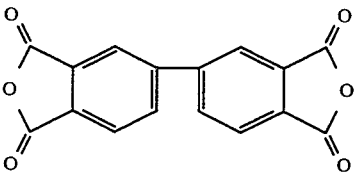

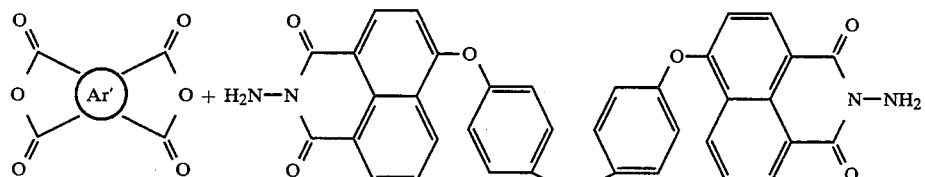

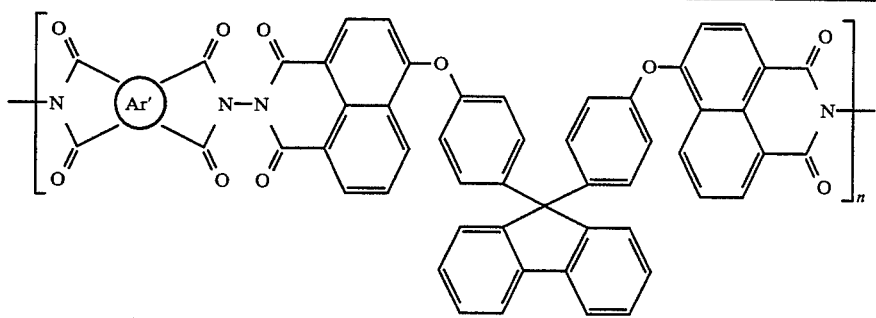

| Anhydride | $T_g$ (°C.) | tan δ (max) (°C.) | Young's modulus (GPa) at | | | TGA (°C.) | | $\eta_{inh}$ dL/g |
|---|---|---|---|---|---|---|---|---|
| | | | 25° C. | 200° C. | 370° C. | $N_2$ | air | |
| ODPA | 398 | 401 | 2.31 | 1.48 | 0.54 | 510 | 520 | 0.44 |
| SDA | 400 | 406 | 2.96 | 2.03 | 0.47 | 500 | 510 | 0.34 |
| BTDA | 404 | 401 | 2.46 | 1.67 | 0.17 | 509 | 521 | 0.45 |

An alternative method of formation of poly(ether imide)s is to first form the imide linkage and then by nucleophilic polymerization with a bisphenoxide form the polymer. For example, reaction of 4-chloro-N-aminophthalimide with 4-chlorophthalic anhydride gives a diimide which by reaction with BPA yields a poly(ether imide).

increasing as the content of the perylenetetracarboxylic diimide moiety increases. Since the simple imides are used as pigments that are photoconductive and are used in xerography in a fashion similar to the phthalocyanines these polymers which are soluble should also be useful in these applications.

Thus the invention also provides a process for producing the polyimides (I) by reacting an imide of formula (XX):

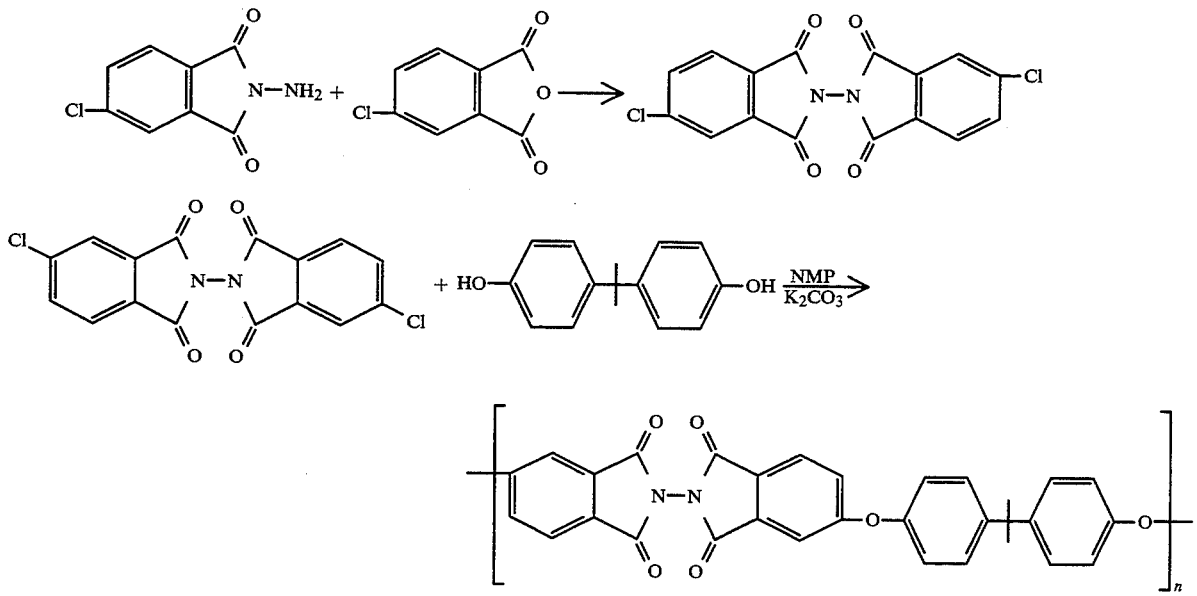

Similarly poly(ether imide)s may be synthesized starting from 4-chloronaphthalic anhydride.

The polymers synthesized from the bis-N-aminoimide of 3,4,9,10-perylenetetracarboxylic dianhydride are intensely red in colour.

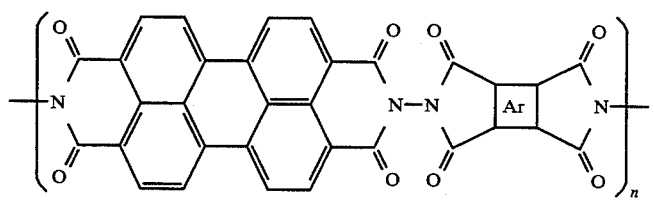

X-Ray diffraction studies have also shown that these polymers are highly crystalline with the crystallinity

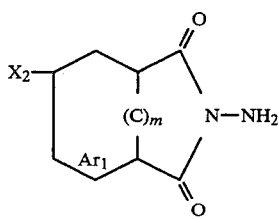

with an anhydride of formula (XI):

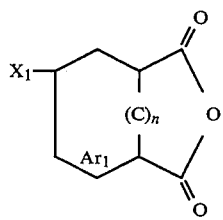

wherein $X_1$ and $X_2$ are the same or different and are fluorine, chlorine, bromine or nitro, and m, n, $Ar_1$ and $Ar_2$ are as described hereinbefore to produce a diimide of formula (IX):

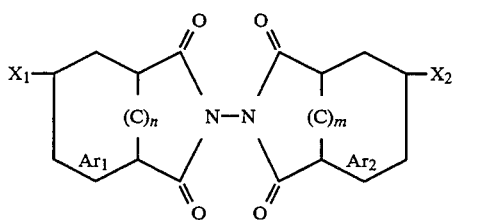

and polymerizing the diamide (IX) with a bisphenol or biphenol.

e) Polymers

The bis-N-aminoimides (III) can also be employed in a variety of polymerization reactions, where diamines are employed, to produce different polymers, for example, polyureas, polyamides, polyetherimides and polyurethanes. In this way there are produced polymers of formula (VII) as described hereinbefore.

The bis-N-aminoimides (III) can also be reacted with bisphenols or biphenols to produce the polymers of formula (II), as described hereinbefore.

In formula (VII) the arylene and aromatic hydrocarbon in $R_1$ and $R_3$ suitably contain 6 to 20 carbon atoms and may include alkyl moieties as part of the 6 to 20 carbon atoms, and may include two or more aromatic nuclei, which nuclei may be fused as in naphylene or non-fused as in biphenylene.

It will be understood that the chemistry for producing these various types of polymers employing diamines is known. The present invention employs the novel bis-N-aminoimides (III) as diamines with beneficial results in the polymers produced, for example, in terms of high glass transition temperatures, solubility, colour, photoconductivity and electroconductivity.

f) Applications

The polymers of the invention, especially those containing the N—N linkage as in formula (I) and (II) are found to have high glass transition temperatures while being soluble in readily available solvents; copolymers incorporating the novel units containing the N—N linkage also have these characteristics.

Thus it would be possible to modify existing commercial polymers such as Ultem ® resin to incorporate therein, during polymerization, the novel N—N containing units of the invention, thereby producing improved polymers of higher glass transition temperature or to increase the solubility of commercial polymers such as Kapton ® resin.

The high glass transition temperatures make the polymers suitable for use in high temperature environments, for example, in industrial and aerospace components.

In view of their solubility the polymers can be cast in films or sheet form from solution, as an alternative to high temperature molding and extrusion operations, thereby simplifying production of parts and components from the polymers.

Many of the polymers are coloured and photoconductive and thus may be fabricated to form fluorescent liquid crystals, microcolour filters and in electrophotography, for example, as charge generating layers and charge transport layers.

The coloured polymers of the invention can be fabricated into these articles, and this represents an advantage over the prior use of single compounds in a composite.

EXPERIMENTAL

Monomer Synthesis

Example 1

4-Chloro-N-amino-1,8-naphthalimide

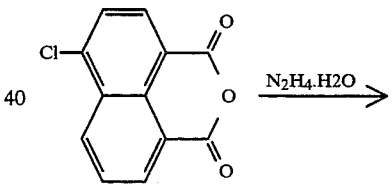

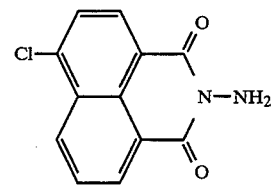

(CNANI)

4-chloro-N-amino-1,8-naphthalimide (CNANI) was prepared by the reaction of hydrazine monohydrate with 4-chloro-1,8-naphthalic anhydride (CNA). First 2.32 g (10 mmole) 4-chloro-1,8-naphthalic anhydride was dissolved in 1300 ml 96% ethanol. To this solution was added 0.5 ml (10 mmol) of hydrazine monohydrate at room temperature. Then 400 mL of solvent was removed by boiling. Upon cooling to room temperature 1.8 g 4-chloro-N-amino-1,8-naphthalimide precipitated in the form of yellow crystals (74% yield): mp 225°–228° C.; 1H NMR (200 MHz, DMSO-d6) δ 6.3 (s, 2H, NH2), 8.5–8.9 (m, 5H, aromatic); MS (EI) m/e calcd for C12H7N2O2Cl: 246.65, found 246.87; 246 (100, M+), 217 (92), 160 (20).

Example 2

2,2-Bis[4-(N-amino,4,5-dicarboxynaphthalimide)-phenyl]propane

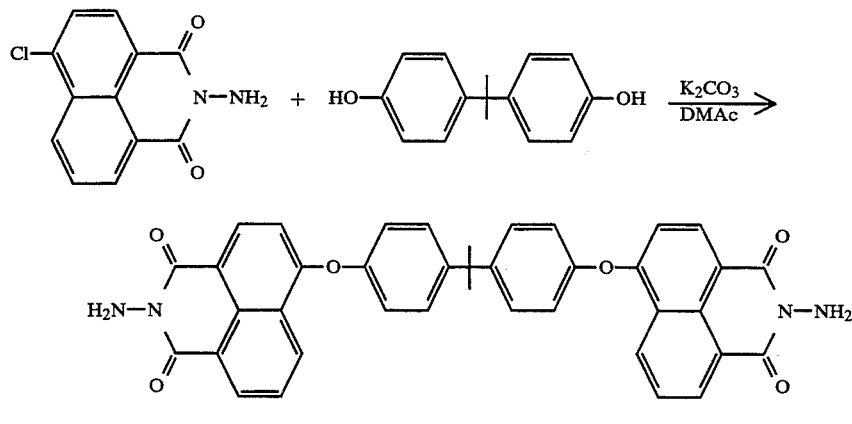

(BPA-BNANI)

In a 100 ml, three-necked flask equipped with a Dean-Stark trap, magnetic stirrer and nitrogen inlet were placed 2.28 g (10 mmol) Bisphenol A (BPA), 3.31 g (24 mmol) anhydrous potassium carbonate, 20 mL dimethyl acetamide (DMAc) and 10 mL toluene. The mixture was heated on an oil bath at 145° C. for 12 h. During this time 12 ml of an azeotropic mixture was removed. After cooling to room temperature, 5.42 g (22 mmol) 4-chloro-N-aminonaphthalimide (CNANI) and 20 mL DMAc were added and the resulting mixture was heated at 80° C. for 24 h during which time all the BPA was used up. The reaction mixture was cooled and extracted by 3×200 mL chloroform. It was washed twice with sodium bicarbonate solution (5%) and once with HCl (5%) then with sodium bicarbonate solution (5%). The organic layer was dried using anhydrous magnesium sulfate and solvent was removed under vacuum. The yellow solid was ground up and washed several times with boiling ethanol (96%) and recrystallized from 1,2-dichlorobenzene to give 4.8 g BPA-BNANI (75% yield): mp 285°–290° C.; $^1$H NMR (200 MHz, CDCl3) δ 1.81 (s, 6H, C(CH3)2), 5.52 (s, 4H, NH2), other aromatic hydrogens are consistent with the structure.; MS (CI with NH3) m/e calcd for C39H28N4O6+H: 649.2090, found 649.2087; 649 (24, MH+), 307 (49), 154 (100), 136 (100).

Example 3

9,9-Bis[4-(N-amino,4,5-dicarboxynaphthalimide)-phenyl]fluorene

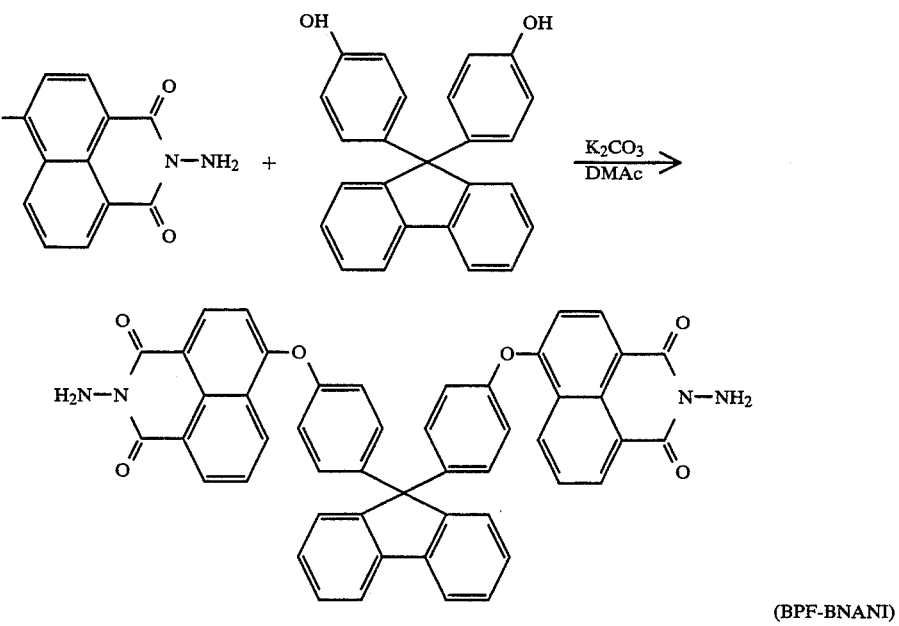

(BPF-BNANI)

A mixture of 3.50 g (10 mmol) bisphenol fluorene (BPF), 3.31 g (24 mmol) anhydrous potassium carbonate, 20 mL dimethylacetamide (DMAc) and 10 mL toluene was heated at 145° C. for 12 h, during which time an azeotropic mixture was removed. After cooling to room temperature, 5.42 g (22 mmol) 4-chloro-N-amino-naphthalimide (CNANI) was added followed by 20 mL of DMAc. The reaction mixture was heated at 80° C. for 24 h and then after cooling down it was extracted using 2×200 mL chloroform. Organic layer was washed twice with sodium bicarbonate solution (5%), once with HCl (5%) then one more time with sodium bicarbonate solution (5%) and dried over anhydrous magnesium sulfate. By removing the chloroform under reduce pressure yellow solid obtained. It was ground up and extracted with ethanol (96%) dried and recrystalized from 1,2-dichlorobenzene to give, after drying, 6.5 g (84% yield) BPF-BNANI: mp 302°–308°C.; $^1$HNMR (CDCl3) δ 4.14 (s, 4H, NH$_2$), other aromatic hydrogens are consistent with the structure. MS (CI with NH3) m/e (calcd for C49H30N4O6+H, 771.2241; found, 771.2243) 771 (41, MH+), 467 (17), 307 (13), 289 (13), 239 (15), 154 (100).

Example 4

2,2-Bis[4-(N-amino,4,5-dicarboxynaphthalimide)-phenyl]hexafluoropropane

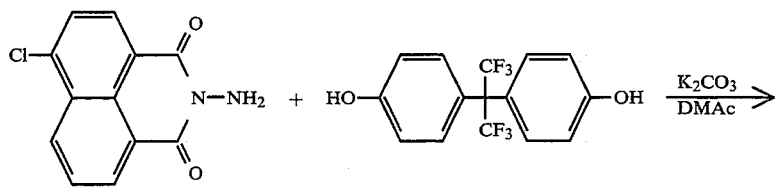

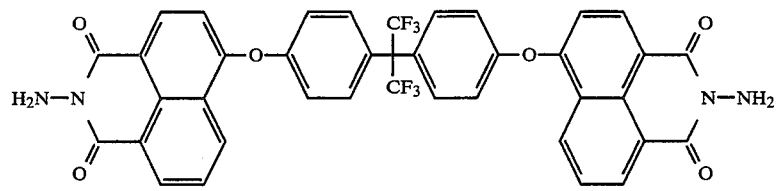

A mixture of 3.36 g (10 mmol) hexafluorobisphenol A (BPA-F6), 3.31 g (24 mmol) anhydrous potassium carbonate, 20 mL dimethylacetamide (DMAc) and 10 mL toluene was heated at 145° C. for 12 h during which time an azeotropic mixture was removed and the bis phenoxide was formed. The reaction mixture was cooled down and 5.42 g (22 mmol) of 4-chloro-N-amino-naphthalimide (CNANI) and 20 mL DMAc were added and the reaction mixture was heated at 80° C. for 12 h. The resulting mixture was cooled and extracted with 3×200 mL chloroform followed by washing twice with sodium bicarbonate solution (5%), once with HCl (5%) and at last with sodium bicarbonate solution (5%). The organic layer was dried over anhydrous magnesium sulfate and removed under vacuum to give crude product. Alter extracting in boiling ethanol (96%) and recrystalising from chlorobenzene, 5.5 g BPA-F6-BNANI obtained as yellow crystals (72% yield): mp 297°–302° C. $^1$HNMR (CDCl3): δ 5.65 (s, 4H, NH2), other aromatic hydrogens am consistent with the structure. MS (CI with NH3) m/e (calcd. for C39H22N4O6F6+H: 757.1521; found, 757.1521) 757 (31, MH+), 154 (100), 136 (73).

Example 5

Naphthalene-N,N'-bis(aminoimide)(BNANI)

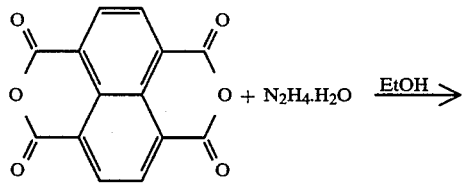

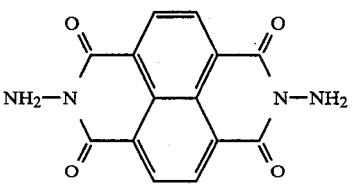

To a solution of 5 g (18.6 mmol) 1,4,5,8-naphthalene tetracarboxylic dianhydride (NDA) in 1 L hot ethanol (96%) was added 2 mL (40 mmol) hydrazine monohydrate. A yellow solid formed which was stirred in boiling ethanol for 4 h to give a light brown colored material which was filtered and dried under vacuum at 100° C. for 24 h. The yield was 4.9 g (90%): mp>400° C., MS (FAB, using nitrobenzyl alcohol (NBA) as matrix and camphorsulfunic acid (CSA) as surfactant) 297 (65, MH+).

Example 6

Perylene-N,N'-bis(aminoimide) (BNAPI)

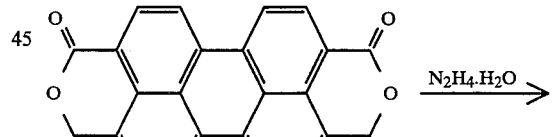

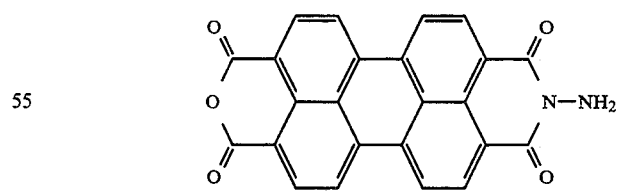

A hydrazine monohydrate (20 mL) solution of 3,4,9,10-perylenetetracarboxylic dianhydride was stirred for 1 h at 50° C. Excess of hydrazine was removed slowly with a flow of nitrogen while the temperature was maintained around 50° C. The resulting solid was dried in vacuum oven at 80° C. for 48 h to give product as dark purple powder in quantitative yield: mp >400° C. MS (FAB, using NBA as matrix and CSA as surfactant) (7.9, MH+).

Example 7
4-Chloro-N-amino phthalimide

Example 8
4,4'-dichloro-N-phthalimidophthalimide

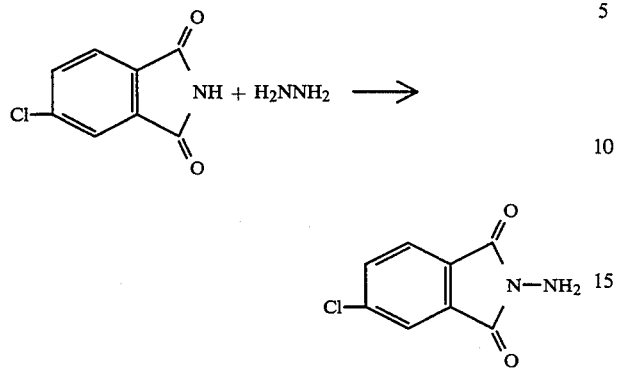

To a cooled mixture of 1.81 g (10 mmol) 4-chloro phthalimide in 20 mL ethanol (96%) was added 0.5 mL (10 mmol) hydrazine monohydrate. The reaction mixture was stirred for 2 min. at room temperature and 2 min. at reflux. By adding 50 mL cold water pale yellow crystals formed alter 1 h. Resulting crystals was filtered and recrystallized from ethanol to give 0.4 g (20%) 4-chloro-N-amino-phthalimide: mp 172°-175° C.; $^1$H NMR (200 MHz, DMSO-d6) d 4.90 (s, 2H, NH2), 7.82-7.92 (m, 3H, C6H3); it solidifies after melting and melts again around 345° C.

To a mixture of 0.44 g (2.4 mmol) 4-chloro phthalic anhydride in glacial acetic acid (10 mL) was added 0.47 g (2.4 mmol) 4-chloro-N-amino-phthalimide. The reaction mixture was refluxed for 30 min. and then it was allowed to cool for several hours. The white solid was filtered and washed with 50 ml ammonium hydroxide solution (5%). The yield was 0.73 g (85%): mp 303°-305° C.; $^1$H NMR (200 MHz, DMSO-d6) d 8.10-8.25 (m, C6H3 ).

Polymers
Preparation of Polyetherimides
Example 9
Polyetherimide from BPA-BNANI and BTDA

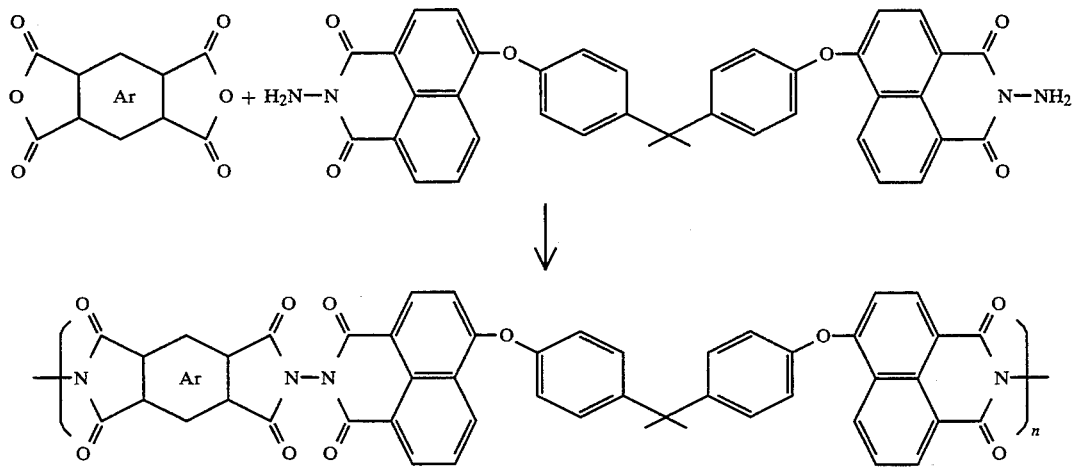

| Anhydride | $T_g$ (°C.) | tan δ (max) (°C.) | Young's modulus (GPa) at | | TGA (°C.) | | Solubility |
| --- | --- | --- | --- | --- | --- | --- | --- |
| | | | 25° C. | 200° C. | N2 | air | |
| PMDA | ND | 380 | 2.22 | 1.92 | 455 | 457 | NMP, o-DCB |
| ODPA | 357 | 340 | 1.81 | 1.48 | 470 | 477 | NMP, PhCl |
| BTDA | 360 | 345 | 2.06 | 1.67 | 454 | 475 | NMP, o-DCB |
| SDA | 362 | 352 | 2.52 | 2.03 | 452 | 466 | NMP, o-DCB |
| BPADA | 307 | 291 | 0.72 | 0.68 | 474 | 467 | CHCl3 |
| BPDA | 375 | 366 | 2.08 | 1.81 | 468 | 478 | NMP, o-DCB |

A typical polymerization example follows: A mixture of 1.0089 g (1.55 mmol) of BPA-BNANI, 0.4962 g (1.54 mmol) of BTDA, 8 mL o-dichlorobenzene 2 mL m-cresol was heated with vigorous stirring at 190°-200° C. for 20 h in a dry nitrogen atmosphere during which time water was removed by azeotropic distillation. The solution became viscous. The polymer solution was diluted with 10 ml o-dichlorobenzene and added slowly to 400 ml methanol giving rise to a fibrous yellow precipitate which was washed thoroughly with methanol, collected by filtration, and dried. The yield was 1.37 g (95%). The inherent viscosity of the polymer in NMP at 60° C. was 0.54 dL/g.

Example 10

Polyetherimide from BPA-BNANI and BPADA

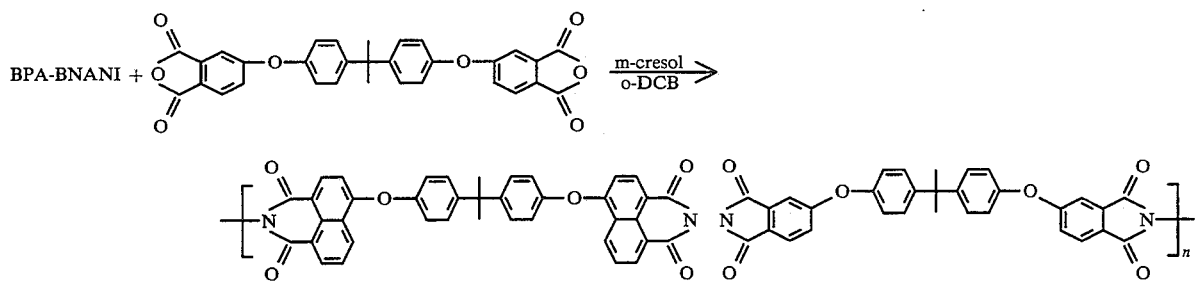

A mixture of 1.0089 g (1.55 mmol) of BPA-BNANI, 0.8015 g (1.54 mmol) of BPADA mad 15 mL o-dichlorobenzene was heated at reflux temperature under nitrogen atmosphere with stirring for 18 h. The reaction mixture was cooled, diluted with 20 mL chloroform and added to methanol to give a precipitate, which was separated and dried under vacuum to give 1.61 g yellow fiber (92% yield).: The inherent viscosity of a 0.5 g/dL polymer solution in NMP was 0.36 dL/g at 60° C.

Example 11

Polyetherimide from BPA-BNANI and ODA

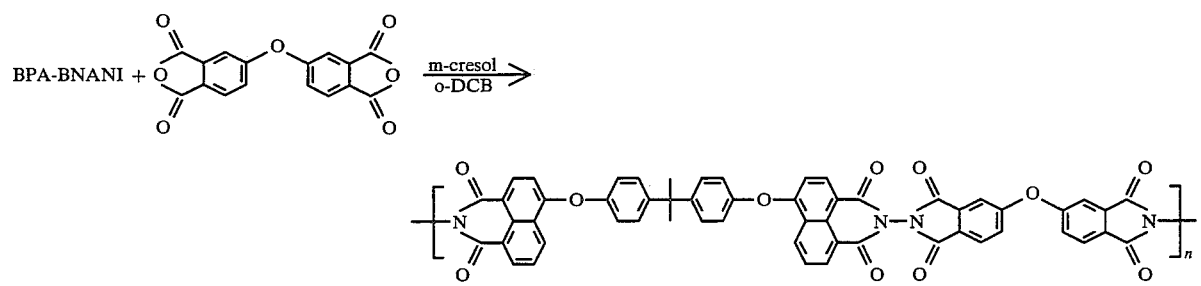

A mixture of 1.0089 g (1.55 mmol) of BPA-BNANI, 0.4962 g (1.54 mmol) of ODA, 8 mL o-dichlorobenzene, 2 ml m-cresol was heated with vigorous stirring at 190°–200° C. for 20 h in a dry nitrogen atmosphere during which time water was removed by azeotropic distillation. The solution became viscous. The polymer solution was diluted with 10 mL of o-dichlorobenzene and tadded dropwise to 400 mL methanol giving rise to a fibrous yellow precipitate which was washed thoroughly with methanol, collected by filtration, and dried. The yield was 1.37 g (95%). The inherent viscosity of a 0.5 g/dL polymer solution in NMP was 0.54 dL/g at 60° C.

Example 12

Polyetherimide from BPA-BNANI) and SDA

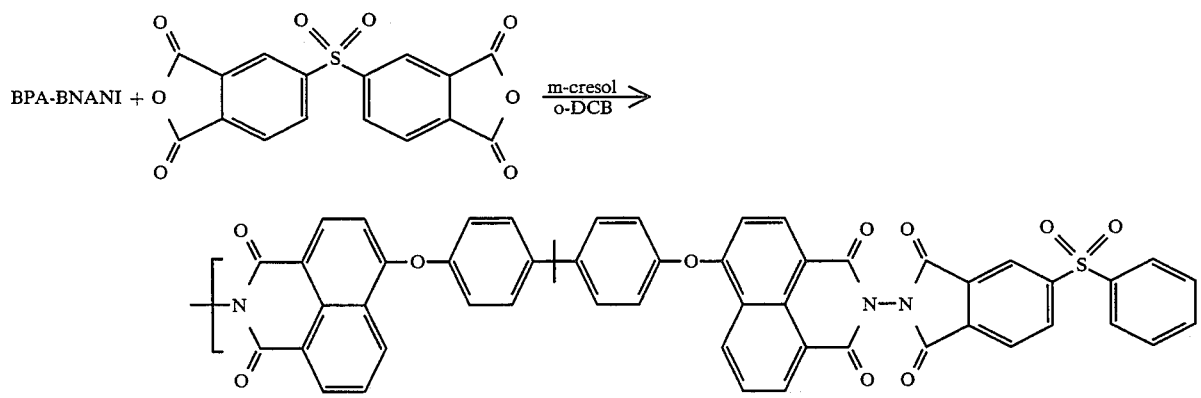

A mixture of 3.0268 g (4.66 mmol) of BPA-BNANI, 1.4330 g (4.62 mmol) of SDA, 15 mL 1o-dichlorobenzene, 15 mL m-cresol was heated with vigorous stirring at 200°–210° C. for 20 h in a dry nitrogen atmosphere during which time water was removed by azeotropic distillation. The resulting viscous, homogeneous polymer solution was diluted with 50 ml 1,2-dichlorobenzene and precipitated in 800 mL methanol giving rise to 4.1 g yellow fibrous polymer (97% yield): The inherent viscosity of a 0.5 g/dL polymer solution in NMP was 0.58 dL/g at 60° C.

Example 13
Polyetherimide BPA-BNANI and BPDA

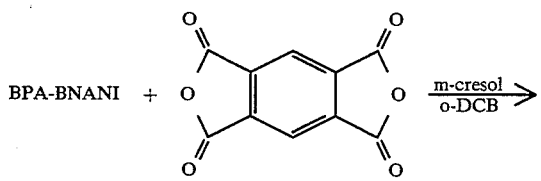

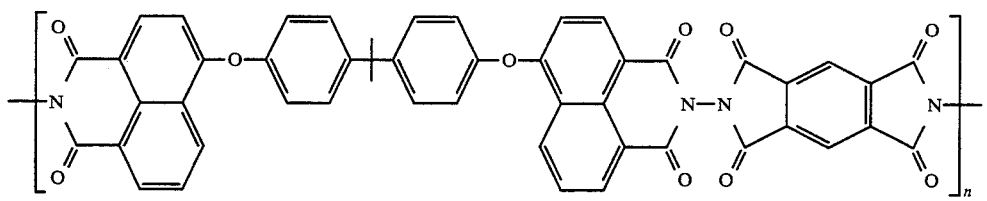

A mixture of 2.9968 g (4.62 mmol) of BPA-BNANI, 1.6552 g (4.62 mmol) of BPDA, 15 mL of o-dichlorobenzene, 15 ml m-cresol was heated with vigorous stirring at 200°–210° C. for 24 h in a dry nitrogen atmosphere during which time water was removed by azeotropic distillation. The solution became viscous. The polymer solution was diluted with 40 mL of o-dichlorobenzene and added dropwise to 800 mL methanol giving rise to a fibrous yellow precipitate which was washed thoroughly with methanol, collected by filtration, and dried. The yield was 4.2 g (93%).: The inherent viscosity of a 0.5 g/dL polymer solution in NMP was 0.37 dL/g at 60° C.

Example 14
Polyetherimide rom BPA-BNANI and PMDA

A mixture of 3.0268 g (4.66 mmol) of BPA-BNANI, 1.0077 g (4.62 mmol) of PMDA, 20 mL o-dichlorobenzene, 15 mL m-cresol was heated with vigorous stirring under nitrogen atmosphere at reflux. Water was removed azeotropically from the reaction mixture. After 20 h, 30 mL of 1o-dichlorobenzene was added and the mixture was cooled to room temperature. The resulting solution was added dropwise to a large excess of methanol. The precipitate was collected by filtration and dried to give 3.5 g polymer (93% yield).: The inherent viscosity of a 0.5 g/dL polymer solution in NMP was 0.47 dL/g at 60° C.

Example 15
Polyetherimide from BPF-BNANI and ODA

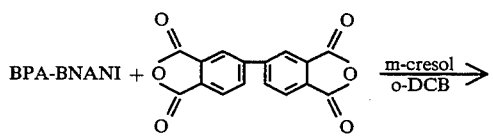

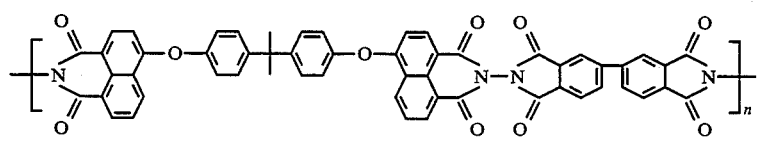

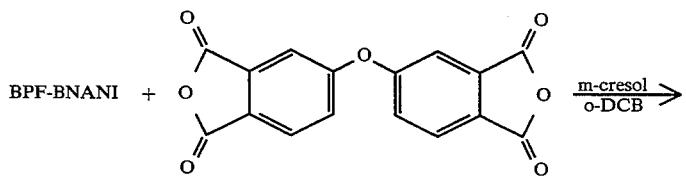

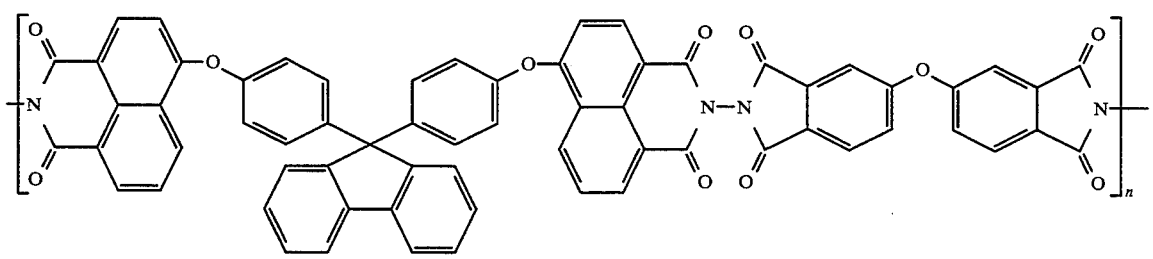

The polyimide was synthesized in the same way as polyetherimides made from BPA-BNANI with 1.2107 g (1.57 mmol) of BPF-BNANI, 0.4782 g (1.54 mmol) of ODA, 8 mL o-dichlorobenzene and 2 mLm-cresol. The reaction mixture was stirred at 190°–200° C. for 24 h under nitrogen during which time water was removed by azeotropic distillation. The resulting polymer solution was diluted with 15 ml 1,2-dichlorobenzene and precipitate into 400 ml methanol. Yellow fibers were collected by filtration and dried under vacuum at 300° C. for 2 h. The yield was 1.5 g (92%).

Example 16

Polyetherimide from N,N'-bis(4-chloronaphthalimido)benzophenone tetracarboxilic bisimide and BPA to give, after drying, 1.65 g (88% yield) product. The inherent viscosity of the polymer in NMP at 60° C. was 0.24 dL/gr.

Example 17

Polyetherimide made from BNANI and BPADA

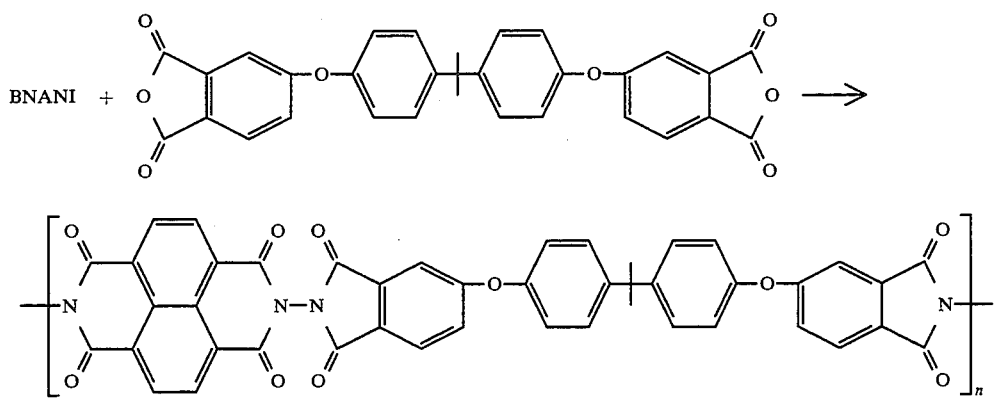

To a stirred solution of 2.6024 g (5.00 mmol) BPADA in a mixture of 6 mL m-cresol and 6 mL 1,2-dichlorobenzene under nitrogen was added 1.5108 g (5.1 mmol) BNANI and 0.0296 g (0.2 mmol) phthalic anhydride. After the reaction mixture was stirred for 1 h, it was heated to reflux (ca. 190°–200° C.) and maintained at that temperature for 6 h. During this time, the water of imidization was allowed to removed azeotropically from the reaction mixture. After the solution was allowed to cool to ambient temperature, it was diluted

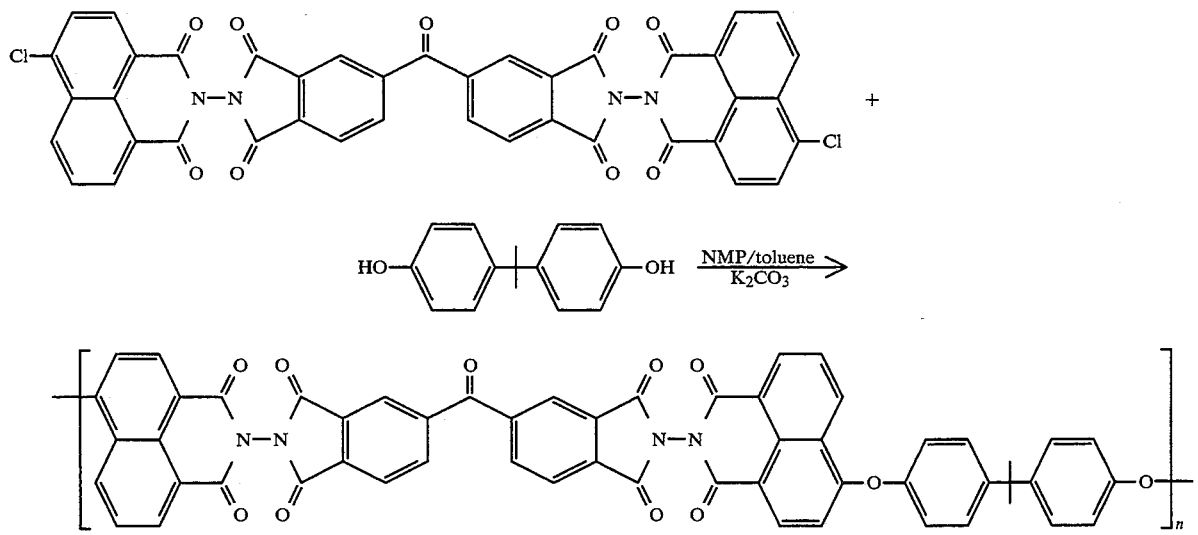

In a 25 mL three-ecked flask equipped with a Dean-Stark trap, magnetic stirrer and nitrogen inlet were added 0.456 g (2 mmol) bisphenol A, 0.332 gr (2.4 mmol) potassium carbonate, 5.5 g NMP and 5 mL toluene. The mixture was stirred under a nitrogen atmosphere for 4 h at about 145° C. after which toluene was removed by distillation. The reaction mixture was cooled down to 50° C. and then 1.556 g (2 mmol) N,N'-bis(4-chloro naphthalimide) benzophenone tetracarboxilic bisimide was added The resulting mixture was stirred at 100° C. for 3 h and after adding 5 ml chlorobenzene it was allowed to cool to room temperature. The resulting polymer was precipitated into methanol with 20 mL 1,2-dichlorobenzene and then slowly added to 800 mL stirred methanol. The precipitated polymer was collected by filtration washed with acetone and dried under reduced pressure at 80° C. for 24 h. The soluble polymer was reprecipitated from chloroform by adding to methanol. The yield was 3.6 g (91%). The inherent viscosity of a 0.5 g/dL polymer solution in chloroform was 0.41 dL/g at 25° C.

Example 18

Copolyetherimide made from BNAPI, BPADA and m-phenylenediamine

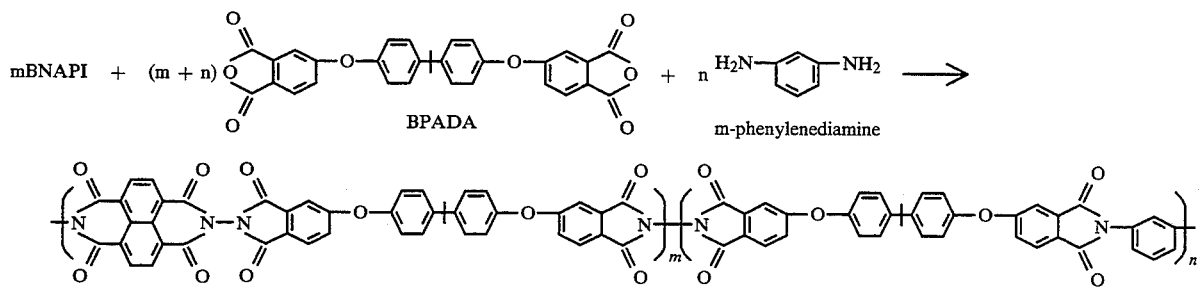

Example 19

Copolyetherimide made from BNAPI, BPADA and m-phenylene diamine

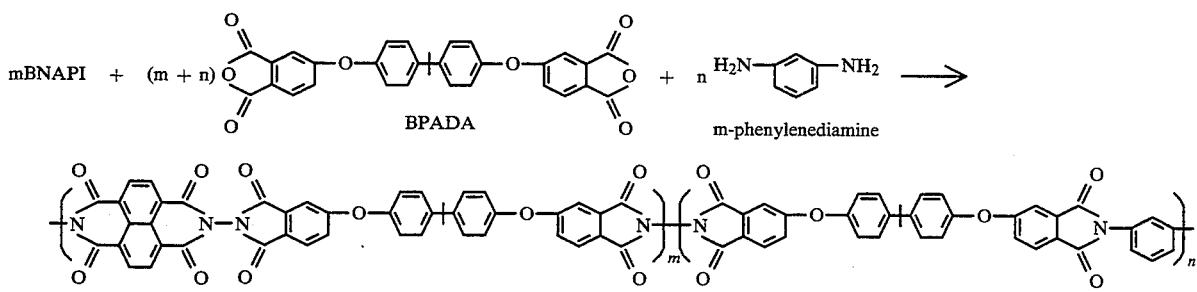

To a stirred solution of 2.0819 g (4.00 mmol) BPADA in a mixture of 5 mL m-cresol and 3 mL of o-dichlorobenzene under nitrogen was added 0.1681 g (0.4 mmol) BNAPI and 0.3893 g (3.6 mmol) m-phenylene diamine. After the reaction mixture was stirred for 1 h, it was heated to reflux (ca. 190°–200° C.) and maintained at that temperature for 6 h. During this time, the water of imidization was removed azeotropically from the reaction mixture. After the solution was allowed to cool to ambient temperature, it was diluted with 20 mL o-dichlorobenzene and then slowly added to 800 mL stirred methanol. The precipitated polymer was collected by filtration and washed with acetone. The soluble polymer was reprecipitated from chloroform with methanol and dried under reduced pressure at 200° C. for 3 h to yield 2.2 g (90%) polymer which is a fuchsia color. The inherent viscosity of a 0.5 g/dL polymer solution in chloroform was 0.21 dL/g at 25° C., To a stirred solution of 2.0819 g (4.00 mmol) BPADA in a mixture of 10 mL m-cresol and 5 mL o-dichlorobenzene under nitrogen was added 0.8576 g (2.04 mmol) BNAPI and 0.2163 g (2.00 mmol) m-phenylene diamine. After the reaction mixture was stirred for 1 h, it was heated to reflux (ca. 190°–200° C.) and maintained at that temperature for 6 h. During this time, the water of imidization was removed azeotropically from the reaction mixture. After the solution was allowed to cool to ambient temperature, it was diluted with 20 mL 1,2-dichlorobenzene and then slowly added to 800 mL of stirred methanol. The precipitated polymer was collected by filtration and washed with acetone. The soluble: polymer was reprecipitated from chloroform with methanol and dried under reduced pressure at 200° C. for 3 h to yield 2.7 g (90%) of red polymer. The inherent viscosity of a 0.5 g/dL polymer solution in TCE was 0.15 dL/g at 35° C.

Example 20

Copolyetherimide made from BNANI, BPADA and BTDA

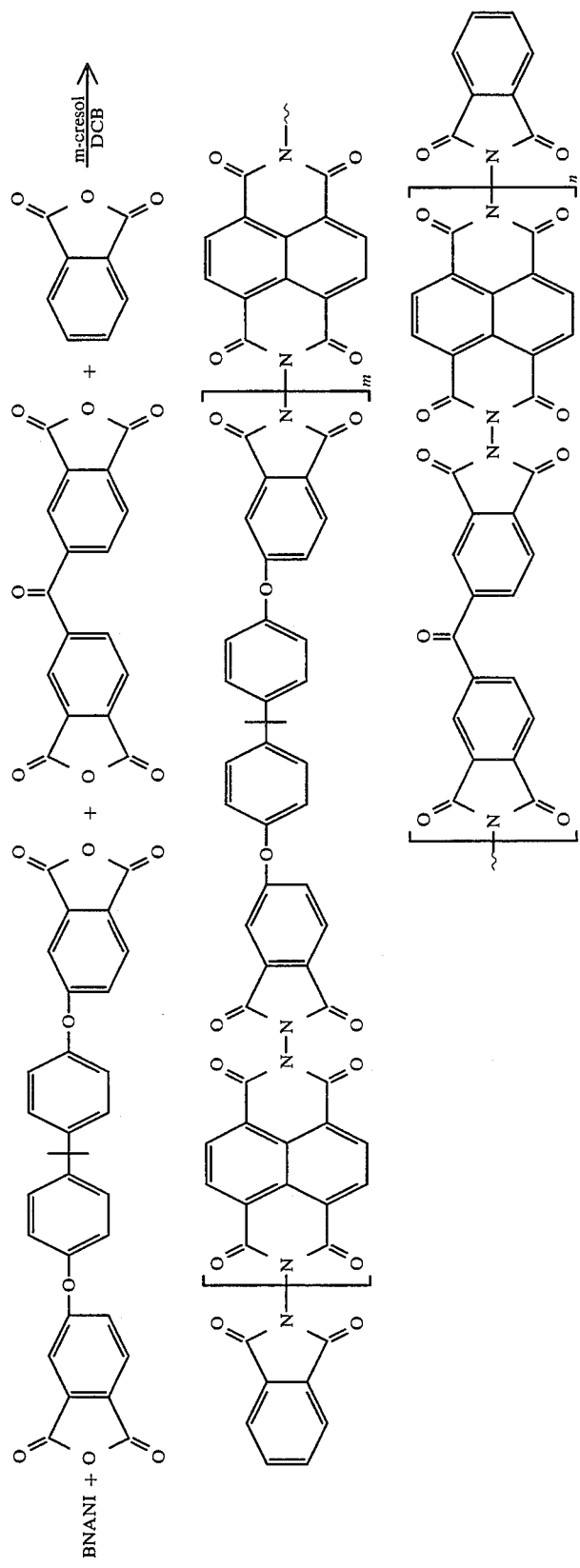

To a stirred solution of 1.0410 g (2.00 mmol) BPADA in a mixture of 5 mL m-cresol and 5 mL 1,2-dichlorobenzene under nitrogen was added 0.9065 g (3.06 mmol) BNANI, 0.3222 g (1.00 mmol) BTDA and 0.0178 g (0.12 mmol) phthalic anhydride. After the reaction mixture was stirred for 1 h, it was heated to reflux (ca. 190°–200° C.) and maintained at that temperature for 6 h. During this time, the water of imidization was allowed to removed azeotropically from the reaction mixture. After the solution was allowed to cool to ambient temperature, it was diluted with 20 mL 1,2-dichlorobenzene and then slowly added to 800 mL stirred methanol. The precipitated polymer was collected by filtration washed with acetone and dried under reduced pressure at 300° C. for 3 h to yield 2.1 g (96%) yellow fibers. The inherent viscosity of a 0.5 g/dL polymer solution in m-cresol was 0.52 dL/g at 50° C.

Example 21

Copolyetherimide made from BNANI, BPADA and ODPA

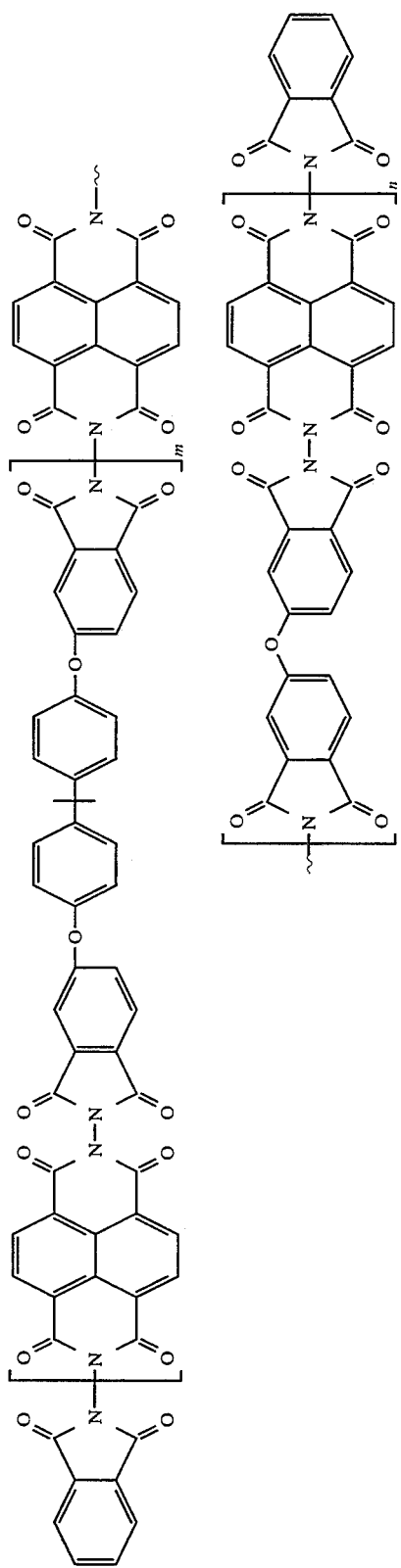
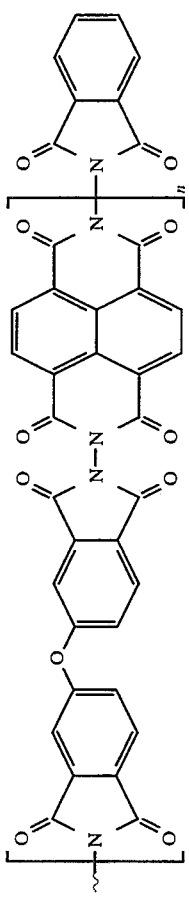

To a stirred solution of 1.0410 g (2.00 mmol) BPADA in a mixture of 5 mL m-cresol and 5 mL 1,2-dichlorobenzene under nitrogen was added 0.9065 g (3.06 mmol) BNANI, 0.3102 g (1.00 mmol) ODPA and 0.0178 g (0.12 mmol) phthalic anhydride. After the reaction mixture was stirred for 1 h, it was heated to reflux (ca. 190°–200° C.) and maintained at that temperature for 6 h. During this time, the water of imidization was allowed to removed azeotropically from the reaction mixture. After the solution was allowed to cool to ambient temperature, it was diluted with 20 mL 1,2-dichlorobenzene and then slowly added to 800 mL stirred methanol. The precipitated polymer was collected by filtration washed with acetone and dried under reduced pressure at 300° C. for 3 h to yield 97% yellow fibers. The inherent viscosity of a 0.5 g/dL polymer solution in m-cresol was 0.66 dL/g at 50° C.

Example 22

Polyetherimide from BPA and 4,4'-dichloro-N-phthalimidophthalimide

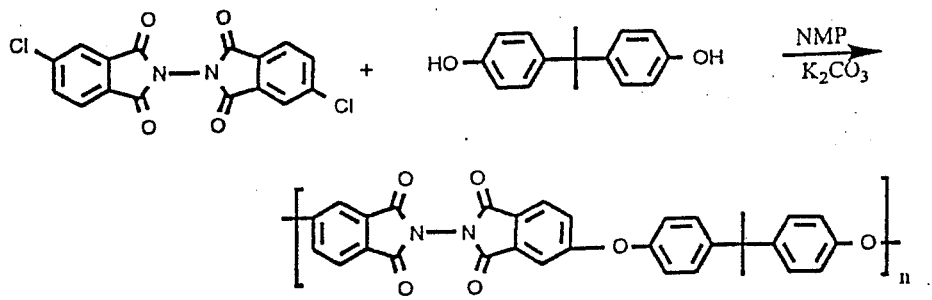

The reaction flask was charged with 0.6849 g (3 mmol) BPA, 0.4146 g (3 mmol) potassium carbonate, NMP (5 mL) and toluene (5 mL). The mixture was then heated under nitrogen until the toluene began to reflux around 130°–140° C. The reaction temperature was maintained at this range until the presence of water was no longer observed in the Dean-Stark trap. The mixture was cooled down to 50° C. and the dichloro monomer was added to the mixture. The temperature raised gradually to 160°–170° C. and maintained at this range for 12 h. The reaction mixture was cooled and precipitated in methanol and filtered, redissolved in chloroform and precipitated in methanol. The resulting material was filtered and dried in a vacuum oven at 90° C. for 48 h to give 1.25 g (80%) polyetherimide. The inherent viscosity of a 0.5 g/dL polymer solution in chloroform was 0.08 dL/g at 25° C.

We claim:

1. A bis-N-aminoimide of formula (III):

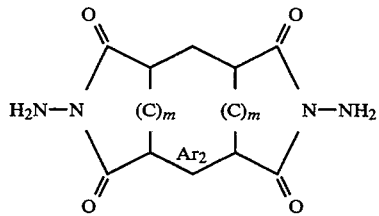

(III)

wherein m is 0 or 1; and

Ar³ is a mono- or polycyclic aromatic radical, provided that when m is 1, Ar³ is other than a naphthalene or perylene radical, and does not include a diazomethine linkage.

2. A bis-N-aminoimide according to claim 1: selected from

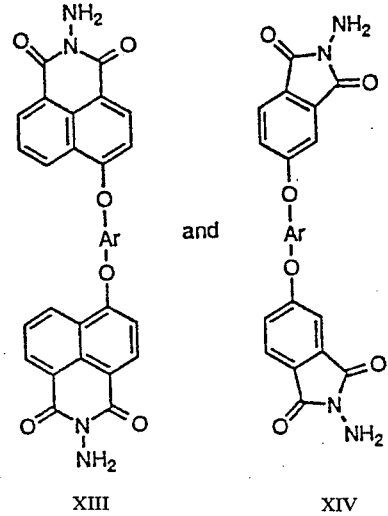

XIII    XIV wherein Ar is an arylene derived from a bisphenol or a biphenol of 12 to 27 carbon atoms.

3. A bis-N-aminoimide of formula (III) according to claim 1 where m is 0 and Ar₂ is a polycyclic aromatic nucleus which comprises 2 non-fused aromatic rings separated by a divalent linkage of formula —O—Ar—O— in which Ar is arylene derived from a bisphenol or a biphenol of 12 to 27 carbon atoms.

4. A bis-N-aminoimide of formula (III) according to claim 3, wherein said non-fused aromatic rings are benzene rings.

5. A bis-N-aminoimide of formula (XIII):

XIII

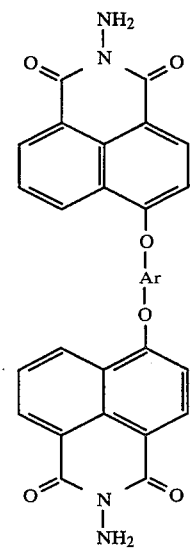

wherein Ar is an arylene derived from a bisphenol or a biphenol of 12 to 27 carbon atoms.

6. A bis-N-aminoimide of formula (XIII) according to claim 5 wherein Ar is derived from a bisphenol of 12 to 27 carbon atoms.

7. A bis-N-aminoimide of formula (XIII) according to claim 5 wherein Ar is derived from a biphenol of 12 to 27 carbon atoms.

8. A bis-N-aminoimide of formula (XIV):

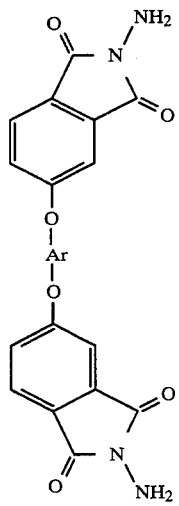

XIV wherein Ar is an arylene derived from a bisphenol or a biphenol of 12 to 27 carbon atoms.

9. A bis-N-aminoimide of formula (XIV) according to claim 8 wherein Ar is derived from a bisphenol of 12 to 27 carbon atoms.

10. A bis-N-aminoimide of formula (XIV) according to claim 8 wherein Ar is derived from a biphenol of 12 to 27 carbon atoms.

* * * * *